(12) United States Patent
Koby et al.

(10) Patent No.: US 8,216,169 B2
(45) Date of Patent: Jul. 10, 2012

(54) WRIST SUPPORT DEVICE

(75) Inventors: Aurelia Koby, San Diego, CA (US); Ian MacMorran, San Diego, CA (US)

(73) Assignee: Brownmed, Inc., Spirit Lake, IA (US)

( * ) Notice: Subject to any disclaimer, the term of this patent is extended or adjusted under 35 U.S.C. 154(b) by 15 days.

(21) Appl. No.: 12/577,954

(22) Filed: Oct. 13, 2009

(65) Prior Publication Data
US 2010/0022930 A1    Jan. 28, 2010

Related U.S. Application Data

(63) Continuation of application No. 11/424,683, filed on Jun. 16, 2006, now abandoned.

(51) Int. Cl.
| A41D 13/08 | (2006.01) |
| A41D 19/00 | (2006.01) |
| A61F 5/37 | (2006.01) |
| A61F 13/00 | (2006.01) |
| A61F 5/00 | (2006.01) |
| A61F 13/06 | (2006.01) |
| A63B 57/00 | (2006.01) |

(52) U.S. Cl. ............... 602/21; 602/5; 602/9; 602/20; 602/60; 602/61; 602/62; 602/63; 602/64; 128/846; 128/869; 128/877; 128/878; 128/879; 2/16; 2/162; 2/910; 473/212; 473/213

(58) Field of Classification Search .................. 602/5, 9, 602/20–22, 60–64; 128/877–880, 846, 869; 2/16, 18, 19, 161.1, 161.2, 161.3, 162, 167, 2/169, 910, 158–161; 473/59–63, 190, 212–213
See application file for complete search history.

(56) References Cited

U.S. PATENT DOCUMENTS
| 5,466,215 | A | 11/1995 | Lair et al. |
| 6,213,969 | B1 | 4/2001 | MacMorran et al. |
| 7,645,250 | B2 | 1/2010 | Koby et al. |

*Primary Examiner* — Patricia Bianco
*Assistant Examiner* — Brandon L Jackson
(74) *Attorney, Agent, or Firm* — McKee, Voorhees & Sease, P.L.C.

(57) ABSTRACT

A wrist support sleeve is adapted to extend over a wearer's hand and wrist from a location below the ends of the fingers tip to a position just past the wrist region. The sleeve has an opening for receiving the wearer's thumb. A first portion of the sleeve extends around the lower part and opposite sides of a wearer's hand and wrist and has spaced side edges located in an upper region of the sleeve. An insert panel of a different material to the first sleeve portion is secured between spaced side edges of the first portion, so as to extend across the tipper portion of a wearer's hand and wrist when the device is worn. The insert panel material is a strong elastic material which has a higher stiffness than the rest of the sleeve.

11 Claims, 2 Drawing Sheets

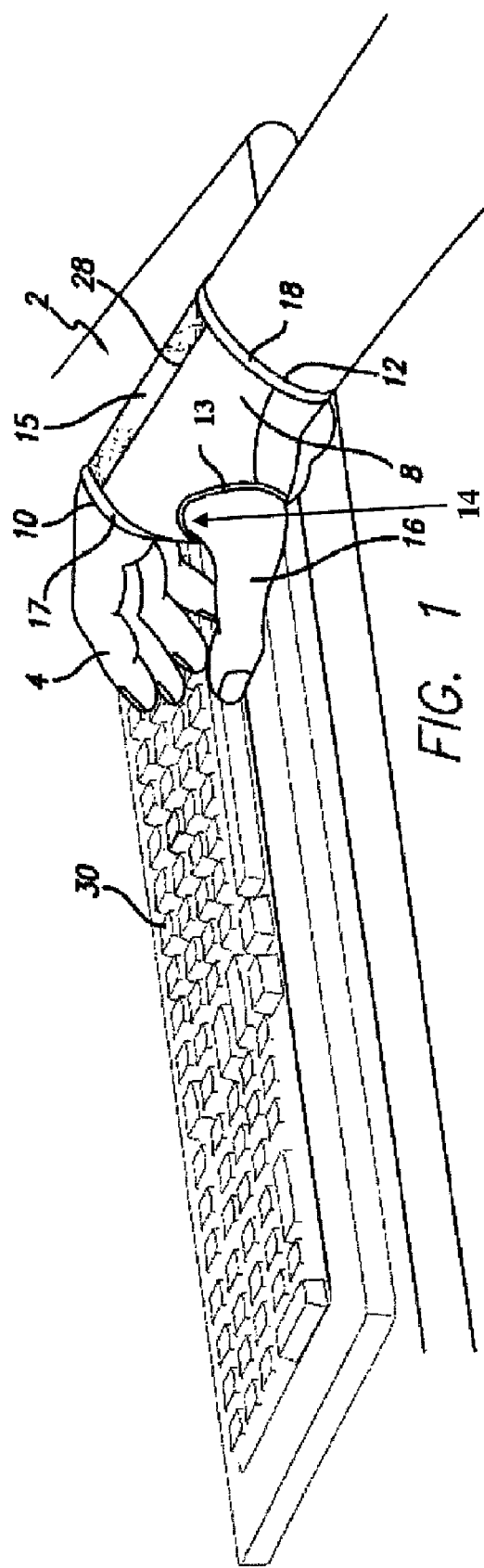
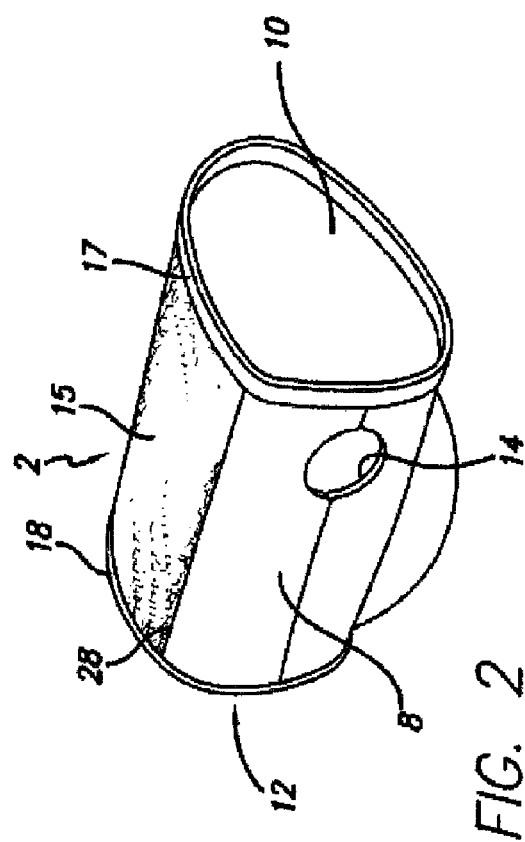
FIG. 1
FIG. 2

WRIST SUPPORT DEVICE

BACKGROUND OF THE INVENTION

This invention relates to a wrist support device for supporting a wearer's wrist in a comfortable position while using a keyboard, laptop computer, personal digital assistant or the like.

Repetitive motion injuries are a common problem among workers who perform repetitive tasks generally, and among typists and computer users in particular. One common injury which can result from excessive keyboard use is carpal tunnel syndrome. Other possible injuries include tendonitis. Arthritis can also make keyboard use difficult. U.S. Pat. No. 6,213,969 of MacMorran et al. describes a wrist support device to alleviate these problems and support the wrist to reduce pain and discomfort when using a keyboard. This device comprises an elongate sleeve with open ends for engaging over a wearer's wrist and the palm of their hand, with a thumb opening on one side. The sleeve is of resiliently stretchable material, and a removable splint of semi rigid material is inserted in a pocket extending along the top of the sleeve, across the wearer's wrist and the back of their hand to provide support. A bead-filled wrist pad is provided in the lower part of the sleeve. The user's wrist will rest on the wrist pad while the keyboard is used, raising the wrist to an ergonomically correct position and cushioning the wrist from the hard surface on which the keyboard rests.

Although the known wrist support device described above is helpful for those who already have some wrist pain or have injuries such as carpal tunnel syndrome, it may be too constraining for other individuals.

SUMMARY OF THE INVENTION

It is an object of the present invention to provide a new and improved wrist support device suitable for more universal use, making keyboard and laptop computer use more comfortable by protecting the wrist from lap top heat and providing cushioning under the surface of the wrist and protecting the sensitive pisiform bone.

According to one aspect of the present invention, a wrist support device is provided, which comprises a sleeve of a first, resiliently stretchable material having opposite open ends and adapted to extend over a user's hand and wrist from a location below the ends of the fingers up to a position past the wrist, the sleeve having an opening for receiving the wearer's thumb, the sleeve being reversible for wear on the user's left or right hand, the sleeve having an upper portion for extending across the top of the wearer's hand and wrist, the upper portion having an insert panel of a second material extending between the opposite open ends of the device, the second material comprising a strong elastic material which is stiffer than the first material.

The second insert panel material may contain a predetermined amount of rubber to provide the desired stiffness and support, and in an exemplary embodiment of the invention this material is 70% polyester and 30% synthetic rubber. The remainder of the sleeve is made of a washable fabric such as a mixture of cotton and stretch fiber material, for example Lycra®. The stiff elastic panel extending over the top of the hand and wrist provides support while still being relatively flexible for comfort.

A bead-filled, moldable pad is mounted in the lower portion of the sleeve at a location that will be beneath the wearer's wrist when the device is worn. This will support the wrist in a comfortable position while using a keyboard, mouse, laptop computer or the like. The length of the sleeve is less than that of the sleeve with a built-in brace as described in U.S. Pat. No. 6,213,969 and the end of the sleeve adjacent the wrist will typically be located in a similar position to a standard glove. This gives the wearer more mobility while wearing the device and is less constraining. The length of the sleeve may be of the order of 3.5 to 5 inches or about 9 to 13 cm.

In one embodiment of the invention, a thumb receiving support or sleeve may extend from the thumb opening. The thumb sleeve will be of the same fabric material as the main sleeve, and may also have an insert panel of the stiffer, rubberized material extending over the top of the thumb. This will be helpful when using devices controlled by the thumb, such as a personal digital assistant or PDA.

The wrist support device of this invention is more of a protective, comfort device for the average user than a therapeutic device for users already experiencing wrist discomfort. The device is shorter than the prior art wrist support to give more mobility, and the elasticated insert panel provides some support across the wrist while being less restrictive than the semi-rigid brace of the prior art device. This device will be particularly useful for wear while traveling, for example when using a laptop computer on an airplane where there is limited space for supporting the wrist and the device provides a stationary wrist rest for the keyboard and mouse.

BRIEF DESCRIPTION OF THE DRAWINGS

The present invention will be better understood from the following detailed description of some exemplary embodiments of the invention, taken in conjunction with the accompanying drawings, in which like reference numerals refer to like parts, and in which:

FIG. 1 is a perspective view of the wrist support device according to a first embodiment of the invention being worn by a user on their right hand while operating a keyboard;

FIG. 2 is a perspective view of the wrist support device alone, showing the device turned inside out to be worn on a user's left hand;

DETAILED DESCRIPTION OF THE DRAWINGS

Figure 3:
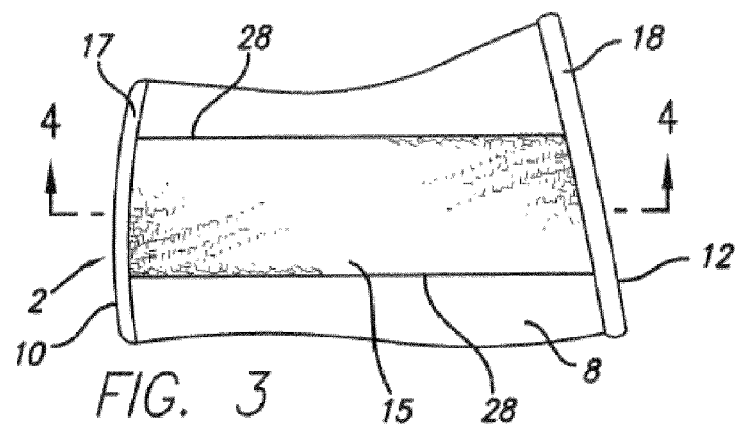
FIG. 3 is a top plan view of the wrist support device.
Figure 4:
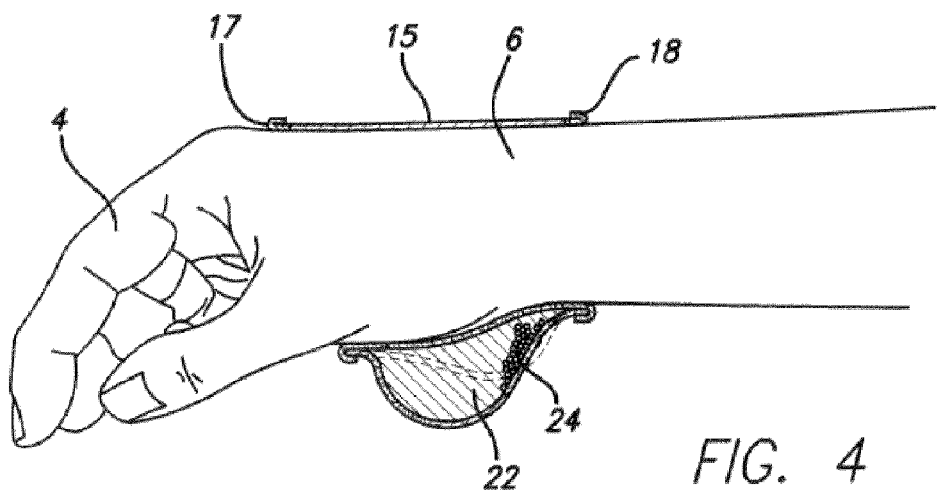
FIG. 4 is a cross section on the lines 4-4 of FIG. 3, illustrating the device being worn.

FIGS. 1 to 4 illustrate a wrist support device 2 according to a first embodiment of the present invention. FIGS. 1 and 4 illustrate the device 2 being worn over a user's hand 4 and wrist 6. The wrist support device basically comprises a sleeve 8 having opposite open ends 10 and 12 and a thumb opening 14 on one side through which the wearer's thumb 16 extends.

A first portion of the sleeve extends around the lower part and sides of the sleeve and is of a stretchable fabric material such as a cotton/Lycra® mixture. A second portion or panel 15 of a stiff elastic material different from the material of the first portion of the sleeve is secured between opposite side edges 28 of the first portion, as best illustrated in FIG. 3. The panel 15 extends along the upper portion of the sleeve between the opposite ends of the sleeve, as illustrated in FIGS. 2 to 4. In an exemplary embodiment of the invention, the insert panel is a mixture of 70% polyester and 30% synthetic rubber. The insert panel is of a much stiffer elastic material than the remainder of the sleeve, and provides support across the top of the wearer's hand and wrist. This will be more comfortable than the rigid or semi rigid brace of some prior art devices by protecting the wrist from lap top heat and providing cushioning under the surface of the wrist and protecting the sensitive pisiform bone.

The opposite open ends and thumb opening of the sleeve may be banded by sewn collars 16, 18 and 20, respectively. The stiff elastic panel 15 is a single layer while the remainder of the sleeve may comprise a double layer, with the elastic panel suitably sewn to the remainder of the sleeve along its opposite side edges 28. As best illustrated in FIG. 4, a moldable pad 22 is attached to a lower portion of the sleeve at a location which is beneath the lower part of the wearer's palm and the wearer's wrist when the device is worn. The pad 22 may be located between the two layers of the sleeve as indicated. The pad is of rounded, cushion-like shape and may comprise an outer pocket or envelope formed integrally within the sleeve and containing a suitable padding material such as foam padding, a filling of small, tightly packed pellets or beads 24, or a gel pack.

The beads 24 filling the moldable pad 22 in the exemplary embodiment of the invention may be formed of plastic material such as low density polyethylene (LDPE) and may be injection molded or extrusion type LDPE particles or pellets. The beads are rounded and free of sharp edges, with a smooth surface which enables the beads to slide smoothly against one another. The beads' surface may be polished to enhance smoothness, and may be coated with a lubricating material and/or a mold suppressant such as an amide. The beads provide a pad which is easily deformable and moldable to the desired position, providing a cushioning effect against any hard surfaces on which the user's wrist would otherwise rest.

When the user wears the wrist support device 2 as illustrated in FIGS. 1 and 4, it can be seen that the moldable pad will provide a cushion for the wearer's wrist and lower palm area as they use a keyboard 30. The keyboard may be part of a laptop or a desktop computer. The wrist support device will also be useful when operating other digital devices such as hand held personal digital assistants. The device 2 is reversible as indicated in FIG. 2, so that it can be turned inside out for wearing on a user's left wrist, and the user can use two wrist support devices, one on each hand.

In an exemplary embodiment, the sleeve length may be in the range from about 3.5 to 5 inches, or around 9 to 13 cm. Since the sleeve 8 is relatively short and does not extend far beyond the wearer's wrist, the user will retain flexibility and mobility while wearing the device. At the same time, the stiffer elastic insert panel 15 which extends across the top of the hand and wrist will provide support and help to keep the wrist in the optimal ergonomic position while operating a keypad or keyboard. This device will be particularly useful and comfortable for wear when using portable electronic devices while traveling, for example when using a laptop computer on an airplane where there is limited space for supporting the wrist and the device provides a stationary wrist rest for the keyboard and mouse.

Figure 5:
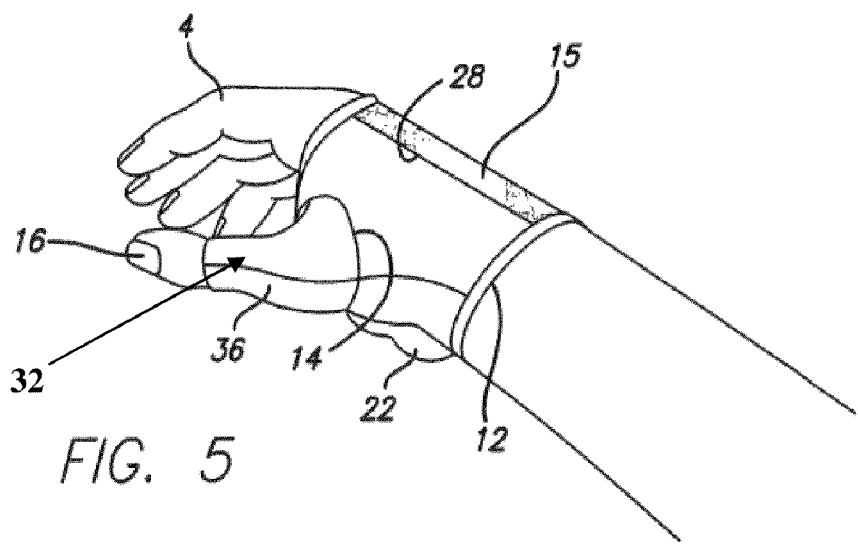
FIG. 5 is a perspective view of a wrist support device according to a second embodiment of the invention being worn by a user.

FIG. 5 illustrates a modification to the device of FIGS. 1 to 4, in which a thumb support sleeve 32 extends from the thumb opening 14. This device is otherwise identical to the device of the previous embodiment, and like reference numerals have been used for like parts as appropriate. The thumb support sleeve 32 may be made entirely of the same material as the majority of the main sleeve 8, or it may also have an insert panel of stiffer elastic material (not illustrated) extending over the top of the thumb for providing more support to the thumb. The panel material in this case will be the same as the material of panel 15. The thumb support sleeve will provide thumb support when operating devices which require thumb actuation, such as personal digital assistants (PDAs) and other handheld devices, games and gaming devices, and the like, while the remainder of the device will help to support the wrist in a comfortable, ergonomic position.

The wrist support device of this invention is less constraining than prior art devices which were longer and extended farther up the arm from the wrist, and which had rigid or semi-rigid brace members extending across the top of the hand and wrist, as in our prior U.S. Pat. No. 6,213,969 referenced above. Such prior art devices are designed more for people who have already suffered wrist injury or who have pain in the wrist or hand from other conditions. The device of this invention is designed for more universal use by anybody using a keypad or keyboard over an extended period of time. The wrist support device is generally shorter in length, terminating just past the wrist region, and has no rigid or semi rigid brace member, but instead has a panel of stiff elastic material for support and comfort. The device is reversible for use on either hand and will be particularly useful when traveling or using portable electronic devices in areas where there is only limited space. The device will both cushion the wrist and lower palm region and provide support across the top of the wrist so as to help maintain a proper ergonomic wrist position. This may help to prevent repetitive motion injuries as well as cushioning and protecting the wrist from hard surfaces and laptop computer heat.

Although some exemplary embodiments of the invention have been described above by way of example only, it will be understood by those skilled in the field that modifications may be made to the disclosed embodiments without departing from the scope of the invention, which is defined by the appended claims.

What is claimed is:

1. A wrist support device, comprising:
a reversible sleeve suitable for either hand having opposite open ends substantially equal in circumference and adapted to extend on a wearer's hand and wrist from a location below the knuckles of the wearer's hand to a position just past the wrist region, the sleeve having an opening for receiving the wearer's thumb, and being without any additional support corresponding to each finger;
the sleeve having a first portion for extending around a lower part and opposite sides of the wearer's hand and having spaced side edges located in an upper region of the sleeve, and a second portion comprising a single-layer insert panel secured between spaced side edges of the first portion wherein the insert panel is integral with and in the same plane as the first portion, the insert panel being adapted to extend across the upper portion of a wearer's hand and wrist when the device is worn;
the first portion of the sleeve being formed of a first material and the insert panel being formed of a second material different from the first material, the first material comprising a stretchable fabric material, and the second material comprising a strong elastic material which has a higher stiffness than the first material, said wrist support being without a batten.

2. The device as claimed in claim 1, wherein the second material comprises a mixture of fabric and natural or synthetic rubber material.

3. The device as claimed in claim 2, wherein the second material comprises a mixture of approximately 70% polyester and 30% synthetic rubber.

4. The device as claimed in claim 1, further comprising a moldable cushioning pad mounted in the lower portion of the sleeve at a location that will be beneath the wearer's wrist when the device is worn.

5. The device as claimed in claim 4, wherein the pad comprises a pocket formed integrally within said sleeve and filled with a plurality of beads.

6. The device as claimed in claim 1, further comprising a thumb receiving sleeve extending from the thumb opening.

7. The device as claimed in claim 6, wherein the thumb receiving sleeve has a second insert panel of the same material as the second material, the second insert panel extending across the top of a wearer's thumb when wearing the device.

8. The device as claimed in claim 1, wherein the first material is a washable fabric.

9. The device as claimed in claim 1, wherein the first material is a mixture of cotton and stretch fiber material.

10. The device as claimed in claim 1, wherein the length of the sleeve is in the range from approximately 3.5 to 5 inches (about 9 to 13 cm).

11. The device of claim 1 wherein the higher stiffness second material is without any separate stiffener element.

\* \* \* \* \*